United States Patent
Wu et al.

(10) Patent No.: US 10,465,177 B2
(45) Date of Patent: Nov. 5, 2019

(54) MALTOOLIGOSYL TREHALOSE TREHALOHYDROLASE (MTHASE) MUTANT AND APPLICATION THEREOF

(71) Applicant: Jiangnan University, Wuxi (CN)

(72) Inventors: Jing Wu, Wuxi (CN); Lingqia Su, Wuxi (CN); Zhendong Wang, Wuxi (CN)

(73) Assignee: Jiangnan University, wuxi, Jiangsu (CN)

( * ) Notice: Subject to any disclaimer, the term of this patent is extended or adjusted under 35 U.S.C. 154(b) by 0 days.

(21) Appl. No.: 15/991,370

(22) Filed: May 29, 2018

(65) Prior Publication Data

US 2019/0249158 A1 Aug. 15, 2019

(30) Foreign Application Priority Data

Feb. 12, 2018 (CN) .......................... 2018 1 0145937

(51) Int. Cl.
  *C12N 9/24* (2006.01)
  *C12P 19/14* (2006.01)
  *C12P 19/12* (2006.01)

(52) U.S. Cl.
  CPC ............ *C12N 9/2402* (2013.01); *C12P 19/12* (2013.01); *C12P 19/14* (2013.01); *C12Y 302/01141* (2013.01)

(58) Field of Classification Search
  CPC ........... C12N 9/2402; C12Y 302/01141; C12P 19/14; C12P 19/12
  See application file for complete search history.

(56) References Cited

PUBLICATIONS

Broun et al., Catalytic plasticity of fatty acid modification enzymes underlying chemical diversity of plant lipids. Science, 1998, vol. 282: 1315-1317. (Year: 1998).*
Chica et al., Semi-rationalapproaches to engineering enzyme activity: combining the benefits of directedevolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Fang et al., Expression, purification, and characterization of the maltooligosyltrehalose trehalohydrolase from thermophilic archaeon Sulfobolus solfataricus ATCC 35092. J. Agric. Food Chem., 2006, vol. 54: 7105-7112 (Year: 2006).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for improving enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*

* cited by examiner

*Primary Examiner* — Ganapathirama Raghu
(74) *Attorney, Agent, or Firm* — IPro, PLLC; Na Xu; Qian Gu (57) ABSTRACT

The present invention discloses a maltooligosyl trehalose trehalohydrolase (MTHase) mutant and application thereof, belonging to the technical fields of gene engineering and enzyme engineering. The present invention provides a series of MTHase mutants to prepare trehalose, having a better effect. Further, the MTHase mutant is expressed in *Escherichia coli* BL21 (DE3) and the enzyme is optimized by fermentation, which can significantly increase the yield of enzymes.

7 Claims, 2 Drawing Sheets

Specification includes a Sequence Listing.

Fig.1

Fig.2

SEQUENCE LISTING

<160> NUMBER OF SEQ ID NOS: 14

<210> SEQ ID NO 1
<211> LENGTH: 1671
<212> TYPE: DNA
<213> ORGANISM: Sulfolobus acidocaldarius

<400> SEQUENCE: 1
atgtttagct ttggcggcaa cattgagaag aataaaggca tctttaagct gtgggcaccg    60

```
tatgtgaata gcgtgaaact gaagctgagc aaaaagctga ttccgatgga gaaaaatgat    120
gaaggctttt ttgaggttga aattgacgat attgaagaaa atctgaccta tagctacatt    180
attgaggaca aacgtgaaat tccggatcca gccagccgtt atcagccgct gggcgtgcat    240
gataagagcc agctgatccg taccgactat caaatcctgg atctgggtaa agtgaaaatc    300
gaagatctga tcatttatga actgcatgtg gtacgtttta gccaggaggg taactttaag    360
ggcgtgatcg aaaaactgga ttacctgaaa gacctgggta tcaccggtat tgaactgatg    420
ccggtggcgc agtttccggg caatcgtgat tggggctatg atggcgtgtt tctgtacgcg    480
gtgcaaaata cctatggcgg tccatgggaa ctggcgaaac tggtgaatga agcgcataaa    540
cgtggcattg cggttattct ggacgtggtt tacaatcata ttggcccaga gggcaattat    600
ctgctgggcc tgggcccgta tttcagcgat cgttataaga cgccgtgggg cctgaccttc    660
aattttgacg accgtggctg cgatcaggtg cgtaaattca tcctggagaa tgtggaatat    720
tggtttaaaa cgttcaagat cgacggcctg cgtctggatg cagtgcatgc gattttttgat    780 aatagcccga acatattcct gcaggaaatc gcggaaaaag cgcaccaact gggcaagttt    840
gtgattgccg aaagcgatct gaatgatccg aaaattgtga aggacgattg tggctacaag    900
attgatgcgc agtgggtgga tgatttccac catgcggtgc atgcgtttat taccaaggaa    960
aaggactact attatcagga ctttggtcgt attgaagaca ttgagaagac gtttaaggat    1020
gtgtttgtgt atgatggcaa atatagccgt tatcgtggtc gcacccatgg tgcgccggtg    1080
ggcgatctgc cgccacgtaa atttgtggtg tttattcaga atcatgacca ggttggcaat    1140
cgtggcaatg gcgaacgtct gagcattctg accgataaaa ccacctatct gatggcggcg    1200
accctgtata ttctgagccc gtatatcccg ctgattttca tgggcgaaga gtattatgaa    1260
accaatccgt tttcttctt cagcgatttt agcgacccgg ttctgatcaa aggtgtgcgt    1320
gagggccgtc tgaaagagaa taaccagatg attgatccgc agagcgagga agcctttctg    1380
aaaagcaaac tgagctggaa aatcgatgag gaagtgctgg attattacaa gcagctgatt    1440
aacatccgta acgttacaa taattgcaaa cgtgtgaaag aagttcgtcg tgaaggtaac    1500
tgcattaccc tgattatgga gaaaattggt attattgcga gctttgatga catcgtgatt    1560
aatagcaaaa ttaccggcaa tctgctgatt ggcattggct ttccgaagaa gctgaaaaaa    1620
gatgaactga ttaaggttaa tcgcggtgtg ggcgtgtatc aactggaata a             1671
```

<210> SEQ ID NO 2
<211> LENGTH: 556
<212> TYPE: PRT
<213> ORGANISM: Sulfolobus acidocaldarius

<400> SEQUENCE: 2

```
Met Phe Ser Phe Gly Gly Asn Ile Glu Lys Asn Lys Gly Ile Phe Lys
1               5                   10                  15

Leu Trp Ala Pro Tyr Val Asn Ser Val Lys Leu Lys Leu Ser Lys Lys
            20                  25                  30

Leu Ile Pro Met Glu Lys Asn Asp Glu Gly Phe Phe Glu Val Glu Ile
        35                  40                  45

Asp Asp Ile Glu Glu Asn Leu Thr Tyr Ser Tyr Ile Ile Glu Asp Lys
    50                  55                  60

Arg Glu Ile Pro Asp Pro Ala Ser Arg Tyr Gln Pro Leu Gly Val His
65                  70                  75                  80

Asp Lys Ser Gln Leu Ile Arg Thr Asp Tyr Gln Ile Leu Asp Leu Gly
```

-continued

```
                85                  90                  95
Lys Val Lys Ile Glu Asp Leu Ile Ile Tyr Glu Leu His Val Gly Thr
                    100                 105                 110

Phe Ser Gln Glu Gly Asn Phe Lys Gly Val Ile Glu Lys Leu Asp Tyr
                    115                 120                 125

Leu Lys Asp Leu Gly Ile Thr Gly Ile Glu Leu Met Pro Val Ala Gln
                130                 135                 140

Phe Pro Gly Asn Arg Asp Trp Gly Tyr Asp Gly Val Phe Leu Tyr Ala
145                 150                 155                 160

Val Gln Asn Thr Tyr Gly Gly Pro Trp Glu Leu Ala Lys Leu Val Asn
                    165                 170                 175

Glu Ala His Lys Arg Gly Ile Ala Val Ile Leu Asp Val Val Tyr Asn
                180                 185                 190

His Ile Gly Pro Glu Gly Asn Tyr Leu Leu Gly Leu Gly Pro Tyr Phe
                    195                 200                 205

Ser Asp Arg Tyr Lys Thr Pro Trp Gly Leu Thr Phe Asn Phe Asp Asp
                210                 215                 220

Arg Gly Cys Asp Gln Val Arg Lys Phe Ile Leu Glu Asn Val Glu Tyr
225                 230                 235                 240

Trp Phe Lys Thr Phe Lys Ile Asp Gly Leu Arg Leu Asp Ala Val His
                    245                 250                 255

Ala Ile Phe Asp Asn Ser Pro Lys His Ile Leu Gln Glu Ile Ala Glu
                260                 265                 270

Lys Ala His Gln Leu Gly Lys Phe Val Ile Ala Glu Ser Asp Leu Asn
                275                 280                 285

Asp Pro Lys Ile Val Lys Asp Cys Gly Tyr Lys Ile Asp Ala Gln
                290                 295                 300

Trp Val Asp Asp Phe His His Ala Val His Ala Phe Ile Thr Lys Glu
305                 310                 315                 320

Lys Asp Tyr Tyr Tyr Gln Asp Phe Gly Arg Ile Glu Asp Ile Glu Lys
                    325                 330                 335

Thr Phe Lys Asp Val Phe Val Tyr Asp Gly Lys Tyr Ser Arg Tyr Arg
                340                 345                 350

Gly Arg Thr His Gly Ala Pro Val Gly Asp Leu Pro Pro Arg Lys Phe
                    355                 360                 365

Val Val Phe Ile Gln Asn His Asp Gln Val Gly Asn Arg Gly Asn Gly
                370                 375                 380

Glu Arg Leu Ser Ile Leu Thr Asp Lys Thr Thr Tyr Leu Met Ala Ala
385                 390                 395                 400

Thr Leu Tyr Ile Leu Ser Pro Tyr Ile Pro Leu Ile Phe Met Gly Glu
                    405                 410                 415

Glu Tyr Tyr Glu Thr Asn Pro Phe Phe Phe Ser Asp Phe Ser Asp
                    420                 425                 430

Pro Val Leu Ile Lys Gly Val Arg Glu Gly Arg Leu Lys Glu Asn Asn
                435                 440                 445

Gln Met Ile Asp Pro Gln Ser Glu Glu Ala Phe Leu Lys Ser Lys Leu
                450                 455                 460

Ser Trp Lys Ile Asp Glu Glu Val Leu Asp Tyr Tyr Lys Gln Leu Ile
465                 470                 475                 480

Asn Ile Arg Lys Arg Tyr Asn Asn Cys Lys Arg Val Lys Glu Val Arg
                    485                 490                 495

Arg Glu Gly Asn Cys Ile Thr Leu Ile Met Glu Lys Ile Gly Ile Ile
                500                 505                 510
```

Ala Ser Phe Asp Asp Ile Val Ile Asn Ser Lys Ile Thr Gly Asn Leu
        515                 520                 525

Leu Ile Gly Ile Gly Phe Pro Lys Lys Leu Lys Lys Asp Glu Leu Ile
    530                 535                 540

Lys Val Asn Arg Gly Val Gly Val Tyr Gln Leu Glu
545                 550                 555

<210> SEQ ID NO 3
<211> LENGTH: 25
<212> TYPE: DNA
<213> ORGANISM: Artificial Sequence
<220> FEATURE:
<223> OTHER INFORMATION: Synthetic DNA

<400> SEQUENCE: 3
gtattgaact gctgccggtg gcgca                                            25

<210> SEQ ID NO 4
<211> LENGTH: 25
<212> TYPE: DNA
<213> ORGANISM: Artificial Sequence
<220> FEATURE:
<223> OTHER INFORMATION: Synthetic DNA

<400> SEQUENCE: 4
tgcgccaccg gcagcagttc aatac                                            25

<210> SEQ ID NO 5
<211> LENGTH: 31
<212> TYPE: DNA
<213> ORGANISM: Artificial Sequence
<220> FEATURE:
<223> OTHER INFORMATION: Synthetic DNA

<400> SEQUENCE: 5
caattatctg ccgggcctgg gcccgtattt c                                     31

<210> SEQ ID NO 6
<211> LENGTH: 31
<212> TYPE: DNA
<213> ORGANISM: Artificial Sequence
<220> FEATURE:
<223> OTHER INFORMATION: Synthetic DNA

<400> SEQUENCE: 6
gaaatacggg cccaggcccg gcagataatt g                                     31

<210> SEQ ID NO 7
<211> LENGTH: 32
<212> TYPE: DNA
<213> ORGANISM: Artificial Sequence
<220> FEATURE:
<223> OTHER INFORMATION: Synthetic DNA

<400> SEQUENCE: 7
cgccgtgggg cgacaccttc aattttgacg ac                                    32

<210> SEQ ID NO 8
<211> LENGTH: 32
<212> TYPE: DNA
<213> ORGANISM: Artificial Sequence
<220> FEATURE:
<223> OTHER INFORMATION: Synthetic DNA

<400> SEQUENCE: 8
gtcgtcaaaa ttgaaggtgt cgccccacgg cg                                    32

<210> SEQ ID NO 9
<211> LENGTH: 35
<212> TYPE: DNA
<213> ORGANISM: Artificial Sequence
<220> FEATURE:
<223> OTHER INFORMATION: Synthetic DNA

<400> SEQUENCE: 9
caaggaaaag gacggctatt atcaggactt tggtc                                 35

<210> SEQ ID NO 10
<211> LENGTH: 35
<212> TYPE: DNA
<213> ORGANISM: Artificial Sequence
<220> FEATURE:
<223> OTHER INFORMATION: Synthetic DNA

<400> SEQUENCE: 10
gaccaaagtc ctgataatag ccgtcctttt ccttg                                 35

<210> SEQ ID NO 11
<211> LENGTH: 33
<212> TYPE: DNA
<213> ORGANISM: Artificial Sequence
<220> FEATURE:
<223> OTHER INFORMATION: Synthetic DNA

<400> SEQUENCE: 11
gacattgaga agacgtctaa ggatgtgttt gtg                                   33

<210> SEQ ID NO 12
<211> LENGTH: 33
<212> TYPE: DNA
<213> ORGANISM: Artificial Sequence
<220> FEATURE:
<223> OTHER INFORMATION: Synthetic DNA

<400> SEQUENCE: 12
cacaaacaca tccttagacg tcttctcaat gtc                                   33

<210> SEQ ID NO 13
<211> LENGTH: 25
<212> TYPE: DNA
<213> ORGANISM: Artificial Sequence
<220> FEATURE:
<223> OTHER INFORMATION: Synthetic DNA

<400> SEQUENCE: 13
gcgaccctgt atactctgag cccgt                                            25

<210> SEQ ID NO 14
<211> LENGTH: 25
<212> TYPE: DNA
<213> ORGANISM: Artificial Sequence
<220> FEATURE:
<223> OTHER INFORMATION: Synthetic DNA

<400> SEQUENCE: 14
acgggctcag agtatacagg gtcgc                                            25

MALTOOLIGOSYL TREHALOSE TREHALOHYDROLASE (MTHASE) MUTANT AND APPLICATION THEREOF

TECHNICAL FIELD

The present invention relates to a maltooligosyl trehalose trehalohydrolase (MTHase) mutant and application thereof, belonging to the technical fields of gene engineering and enzyme engineering.

BACKGROUND

Trehalose is composed of two glucopyranose molecules linked by an α, α-1,1-glycosidic bond. It is a stable non-reducing disaccharide, with high safety and good stability. It is widely used in the fields of medicine, food, makeup and agriculture, etc. Since 1995, trehalose has been approved as a food additive in Japan, the United States, the European Union, etc. In 2005, trehalose was officially approved as a new resource food by the Ministry of Health of P. R. China.

In 1993, Hayashibara Biochemical Labs first discovered that the maltooligosyl trehalose synthase (MTSase) and maltooligosyl trehalose trehalohydrolase (MTHase) could be used to produce trehalose through the synergistic effect thereof by using liquefied starch as a substrate, and first achieved the industrial production of trehalose. At present, some enterprises in China have started to produce trehalose, but the product performance and yield are still inferior to imported products and the production costs remain high. What is more challenged is that the selling price of trehalose continues to drop to meet the market demands, which bringing great challenge and pressure for the production of trehalose. Therefore, how to increase the yield of trehalose, achieve large-scale production of trehalose at low cost, and provide it to massive common consumers's tables has become a hot issue in the academic and industrial circles.

At present, the industrial production of trehalose is mainly through two methods: (1) using trehalose synthase, and using maltose as a substrate to generate trehalose through intramolecular transglycosylation; (2) using starch liquefaction liquid as a substrate to produce trehalose through the synergistic effect of MTSase and MTHase. The two methods can achieve the similar yield of trehalose. However, considering the production cost and the cycle, it is more convenient and inexpensive to produce trehalose by using starch as a substrate. Therefore, the production of trehalose through the synergistic effect of MTSase and MTHase is more advantageous.

The double enzymatic method used at home and abroad includes medium-low temperature enzyme systems (source strains include *Arthrobacter* sp. Q36, *Arthrobacter ramosus* S34, *Brevibaterium helvolum*, etc.) and high temperature enzyme systems (source strains include *Sulfolobus solfataricus* KM1 and *Sulfolohus acidocaldarius* ATCC 33909, etc.). The high temperature enzyme systems usually have a high trehalose conversion rate, and have high thermal stability. They can convert starch to trehalose at a relatively high temperature, and it is not easy to contaminate bacteria during the production process. However, compared with the medium-low temperature enzyme systems, the high-temperature enzyme systems have low protein expression level, which is not conducive to their industrial applications.

SUMMARY

Based on the current situation, the present invention utilizes genetic engineering and enzyme engineering methods to increase the enzyme activity of MTHase and create conditions for its industrial production.

The present invention provides a mutant, with increased enzyme activity, of MTHase, comprising a mutant obtained by substituting one or more of amino acids at positions 140, 202, 218, 323, 338, or 404 of an MTHase derived from *Sulfolobus acidocaldarius*. Compared to their parent MTHase, these mutants have increased enzyme activity.

In one embodiment of the present invention, the amino acid sequence of the MTHase derived from *Sulfolobus acidocaldarius* is shown in SEQ ID NO.2. A nucleotide sequence encoding the gene of the MTHase derived from *Sulfolobus acidocaldarius* is shown in SEQ ID NO.1.

In one embodiment of the present invention, the mutant is obtained by mutating methionine (Met) at position 140 to leucine (Leu), and the mutant is named M140L.

In one embodiment of the present invention, the mutant is obtained by mutating leucine (Leu) at position 202 to proline (Pro), and the mutant is named L202P.

In one embodiment of the present invention, the mutant is obtained by mutating leucine (Leu) at position 218 to aspartic acid (Asp), and the mutant is named L218D.

In one embodiment of the present invention, the mutant is obtained by mutating tyrosine (Tyr) at position 323 to glycine (Gly), and the mutant is named Y323G.

In one embodiment of the present invention, the mutant obtained by mutating phenylalanine (Phe) at position 338 to serine (Ser), and the mutant is named F338S.

In one embodiment of the present invention, the mutant is obtained by mutating isoleucine (Ile) at position 404 to threonine (Thr), and the mutant is named I404T.

In one embodiment of the present invention, the mutant is obtained by mutating leucine (Leu) at position 202 to proline (Pro), and obtained by mutating tyrosine (Tyr) at position 323 to glycine (Gly), to obtain L202P/Y323G.

In one embodiment of the present invention, the mutant is obtained by mutating leucine (Leu) at position 202 to proline (Pro), mutating leucine at position 218 (Leu) to aspartic acid (Asp), and mutating tyrosine (Tyr) at position 323 to glycine (Gly), to obtain L202P/L218D/Y323G.

In one embodiment of the present invention, the mutant is obtained by mutating methionine (Met) at position 140 to leucine (Leu), mutating leucine at position 202 (Leu) to proline (Pro), mutating leucine (Leu) at position 218 to aspartic acid (Asp), and mutating tyrosine (Tyr) at position 323 to glycine (Gly), to obtain M140L/L202P/L218D/Y323G.

In one embodiment of the present invention, the mutant is obtained by mutating methionine (Met) at position 140 to leucine (Leu), mutating leucine (Leu) at position 202 to proline (Pro), mutating leucine (Leu) at position 218 to aspartic acid (Asp), mutating tyrosine (Tyr) at position 323 to glycine (Gly), and mutating phenylalanine (Phe) at position 338 to serine (Ser), to obtain M140L/L202P/L218D/Y323G/F338S.

In one embodiment of the present invention, the mutant is obtained by mutating methionine (Met) at position 140 to leucine (Leu), mutating leucine (Leu) at position 202 to proline (Pro), mutating leucine (Leu) at position 218 to aspartic acid (Asp), mutating tyrosine (Tyr) at position 323 to glycine (Gly), mutating phenylalanine (Phe) at position 338 to serine (Ser), and mutating isoleucine (Ile) at position 404 to threonine (Thr), to obtain M140L/L202P/L218D/Y323G/F338S/I404T.

In order to solve another technical problem, the present invention provides a method for preparing a MTHase mutant, comprising the following steps:

(1) designing a site-directed mutagenic primer based on a determined mutation site, and carrying out site-directed mutagenesis by using a vector carrying an MTHase gene as a template; constructing a plasmid vector containing the gene encoding the mutant;

(2) transforming a mutant plasmid into a host cell; and (3) picking out a positive clone for fermentation, and collecting cells by centrifugation, wherein cell wall breaking supernatant is a crude enzyme solution of the mutant MTHase.

In one embodiment of the present invention, the plasmid vector is any one of pET series, pUC series or pGEX.

The host cell is a bacterial cell or a fungal cell.

The bacteria are gram-negative bacteria or gram-positive bacteria.

The third objective of the present invention is to provide a method for producing MTHase by using recombinant *Escherichia coli* expressing the mutant. The method comprises the steps: inoculating a fermentation medium with recombinant bacteria carrying the gene encoding the mutant M140L/L202P/L218D/Y323G/F338S/I404T, culturing at 37° C. for 8 to 14 hours, adding lactose at a flow rate of 0.1 g L$^{-1}$ h$^{-1}$, and performing induction at 30° C. for 10 to 20 hours.

In one embodiment of the present invention, the induction is performed at 30° C.

In one embodiment of the present invention, the method comprises the steps: inoculating an LB medium with the strains stored in a glycerol tube at −80° C. at an inoculation amount of 2%0, and culturing for 10 hours under the conditions of 200 rpm and 37° C.; subsequently, transferring to a fermentation medium with an inoculation amount of 5%, culturing at 37° C. for 8 to 14 hours, performing induction by adding an inductive agent, changing the temperature, and continuing to ferment; and after fermentation culture, centrifuging, collecting the bacteria, performing wall breaking, centrifuging to obtain supernatant, namely a desired crude enzyme solution.

In one embodiment of the present invention, the wall breaking is performed by a sonicator or a high-pressure homogenizer.

In one embodiment of the present invention, the fermentation medium per liter contains 4.0 g of diammonium phosphate, 13.5 g of potassium dihydrogen phosphate, 1.7 g of citric acid, 1.4 g of magnesium sulfate heptahydrate, 1.2 g of peptone, 2.4 g of yeast extract, 8.0 g of glycerol, and 10 mL of metal ion liquid, and the pH is adjusted to 6.5 to 7.5 by adding ammonia water. The metal ion liquid is prepared from FeSO$_4$.7H$_2$O 10 g/L, ZnSO$_4$.7H$_2$O 2.25 g/L, CuSO$_4$.5H$_2$O 1.0 g/L, MnSO$_4$.4H$_2$O 0.5 g/L, Na$_2$B$_4$O$_7$.10H$_2$O 0.23 g/L, CaCl$_2$ 2.0 g/L, and (NH$_4$)$_6$Mo$_7$O$_2$4 0.1 g/L by taking 5M HCl as mother liquor.

The present invention provides a series of MTHase mutants with increased enzymatic activity in a host strain. Under appropriate culture conditions, the enzyme activities of the mutants M140L, L202P, L218D, Y323G, F338S, I404T, L202P/Y323G, L202P/L218D/Y323G, M140L/L202P/L218D/Y323G, M140L/L202P/L218D/Y323G/F338S, and M140L/L202P/L218D/Y323G/F338S/I404TMTHases are 1.3, 1.3, 1.3, 1.3, 1.5, 1.0, 1.5, 1.9, 2.2, and 2.4 times those of wild type enzymes, respectively. In addition, the K$_m$ value of the mutant M140L/L202P/L218D/Y323G/F338S/I404T is lower than that of the wild type enzyme, indicating that the affinity of the mutant to the substrate is enhanced.

DETAILED DESCRIPTION

Example 1: Expression of Wild Type MTHase

An LB liquid medium (containing 100 mg/L kanamycin) is inoculated with Tre Z/pET24a(+)/BL21 (DE3) stored in a glycerol tube in the laboratory for growth for 8 h, and a TB liquid fermentation medium (containing 100 mg/L kanamycin) are inoculated with seeds according to 5% of inoculation amount. After *Escherichia coli* is cultured in a shaker at 25° C. for 24 h, a certain volume of fermentation broth is centrifuged at 4° C. and 12,000 rpm for 10 min. The supernatant is discarded to collect the bacteria, then the bacterial precipitate is resuspended with 20 mmol·L$^{-1}$ Na$_2$HPO$_4$—NaH$_2$PO$_4$ buffer of pH 8.0, and mixed well. The cell wall of the bacterial suspension is broken by an ultrasonic cell disrupter (the operating conditions of the ultrasonic cell disrupter: ψ6 operating probe, operating time 10 min, operating for 2 s and stopping for 3 s, and the operating power 20%), and then centrifuging is performed at 12,000 rpm for 10 min. After centrifugation, the supernatant is a fermented intracellular crude enzyme solution.

Example 2: Preparation and Expression of MTHase Single Mutant (1) Preparation of Mutant Primers into which M140L, L202P, L218D, Y323G, F338S, and 1404T mutations are introduced are designed and synthesized according to the gene sequence of *Sulfolobus acidocaldarius* MTHase, and site-directed mutagenesis of the MTHase gene Tre Z is carried out, and sequencing is carried out respectively to confirm whether the MTHase mutant encoding genes are correct; a vector carrying the mutant gene is introduced into *Escherichia coli* for expression, to obtain a single mutant MTHase.

PCR amplification of encoding genes of site-directed mutant comprises: a rapid PCR technique is adopted, and the expression vector Tre Z/pET-24a(+) carrying the genes encoding the wild type MTHase as a template.

The site-directed mutagenic primers into which M140L mutation is introduced are as follows:

```
Forward primer:
5'-GTATTGAACTGCTGCCGGTGGCGCA-3' (SEQ ID NO. 3,
underlined as mutant bases); and Reverse primer:
5'-TGCGCCACCGGCAGCAGTTCAATAC-3' (SEQ ID NO. 4,
underlined as mutant bases).
```

The site-directed mutagenic primers into which L202P mutation is introduced are as follows:

```
Forward primer:
5'-CAATTATCTGCCGGGCCTGGGCCCGTATTTC-3'
(SEQ ID NO. 5,
underlined as mutant bases); and Reverse primer:
5'-GAAATACGGGCCCAGGCCCGGCAGATAATTG-3'
(SEQ ID NO. 6,
underlined as mutant bases).
```

The site-directed mutagenic primers into which L218D mutation is introduced are as follows:

```
Forward primer:
5'-CGCCGTGGGGCGACACCTTCAATTTTGACGAC-3'
(SEQ ID NO. 7, underlined as mutant
bases); and Reverse primer:
5'-GTCGTCAAAATTGAAGGTGTCGCCCCACGGCG-3'
(SEQ ID NO. 8, underlined as mutant
bases).
```

The site-directed mutagenic primers into which Y323G mutation is introduced are as follows:

```
Forward primer:
5'-CAAGGAAAAGGACGGCTATTATCAGGACTTTGGTC-3'
(SEQ ID NO. 9, underlined as mutant bases);
and Reverse primer:
5'-GACCAAAGTCCTGATAATAGCCGTCCTTTTCCTTG-3'
(SEQ ID NO. 10, underlined as mutant bases).
```

The site-directed mutagenic primers into which F338S mutation is introduced are as follows:

```
Forward primer:
5'-GACATTGAGAAGACGTCTAAGGATGTGTTTGTG-3'
(SEQ ID NO. 11, underlined as
mutant bases); and Reverse primer:
5'-CACAAACACATCCTTAGACGTCTTCTCAATGTC-3'
(SEQ ID NO. 12, underlined as mutant
bases).
```

The site-directed mutagenic primers into which I404T mutation is introduced are as follows:

```
Forward primer:
5'-GCGACCCTGTATACTCTGAGCCCGT-3' (SEQ ID NO. 13,
underlined as mutant bases); and Reverse primer:
5'-ACGGGCTCAGAGTATACAGGGTCGC-3' (SEQ ID NO. 14,
underlined as mutant bases).
```

PCR reaction system are all as follows: 5×PS buffer 10 µL, dNTPs Mix (2.5 mmol·L$^{-1}$) 4 µL, forward primer (10 µmol·L$^{-1}$) 1 µL, reverse primer (10 µmol·L$^{-1}$) 1 µL, template DNA 1 µL, and PrimeStar HS (5 U/µL) 0.5 µL; distilled water is added to achieve 50 µL.

PCR procedure comprises the steps: first, performing denaturation at 94° C. for 4 min; then starting 30 cycles: denaturation at 98° C. for 10 s, annealing at 55° C. for 5 s, and extension at 72° C. for 7 min 20 s; finally performing extension at 72° C. for 10 min, performing heat perservation at 4° C. The PCR product is detected by 1% agarose gel electrophoresis.

After the correct PCR product is verified, Dpn I is added to the PCR product, water bath is performed at 37° C. for 2 h to degrade the template. Afterwards, *Escherichia coli* JM109 competent cells are transformed and the transformed product is used for coating an LB solid medium containing 100 mg/L kanamycin, and culturing is performed at 37° C. for 10 to 12 h. Positive clones are selected and cultured in an LB liquid medium for 8 to 10 h. The correct mutants are sequenced, and an LB medium is inoculated from a glycerol tube, and culturing is performed overnight. Plasmids are extracted and transformed to express host *Escherichia coli* BL21 (DE3) competent cells, so as to obtain recombinant strains that can express mutants M140L, L202P, L218D, Y323G, F338S and I404T.

(2) Expression of Mutants

The mutant expression process is described as that in Example 1.

Example 3: Analysis of MTHase Enzyme Activity

Enzyme activity is defined as the amount of enzyme required to produce one micromole of maltooligosaccharides per minute.

Determination of enzyme activity comprises the steps: preheating: taking 0.45 mL of 2% maltodextrin solution (DE 9 to 13 pH 6.0 phosphate buffer) in a test tube and placing in a 60° C. water bath to preheat for 10 min; reaction: adding 0.05 mL of diluted fermented intracellular crude enzyme solution, shaking well, for 10 min (accurate timing), then adding 0.1 mL of NaOH solution (4 mol/L) to terminate the reaction, and taking 0.3 mL of reaction solution in a test tube with a stopper, then adding 0.7 mL of distilled water and 4 mL of DNS, shaking well to stop the reaction, then boiling for 7 min and cooling; measurement: adding distilled water to the above reaction system to a constant volume of 15 mL, mixing well, measuring the absorbance at the wavelength of 540 nm and calculating the enzyme activity.

$OD_{600\ nm}$ of shake flask culture for 24 h and enzyme activity of the wild type MTHase (WT) and mutants are listed in Table 1. The results show that all the mutants have higher enzyme activity than the wild type.

TABLE 1

$OD_{600\ nm}$ of shake flask and enzyme activity of wild type MTHase and single mutant enzyme

| Enzyme | $OD_{600\ nm}$ | Enzyme activity (U/mL) |
|---|---|---|
| WT | 12.9 | 31.2 |
| M140L | 12.7 | 39.9 |
| L202P | 12.1 | 41.9 |
| L218D | 12.9 | 40.9 |
| Y323G | 12.2 | 42.9 |
| F338S | 11.5 | 47.7 |
| I404T | 10.5 | 30.2 |

Example 4: Preparation, Expression and Enzyme Activity Analysis of MTHase Double Mutant By using the plasmid of the mutant L202P constructed in Example 2 as a template for double mutation and according to site-directed mutagenic primers designed in Example 2, site-directed mutagenesis is performed on the plasmid carrying the genes encoding the mutant L202P through a rapid PCR technique, so as to construct a double mutant L202P/Y323G. Sequencing is performed to identify whether the encoding genes of MTHase double mutant are correct, and the plasmid with correct sequencing result is introduced into *Escherichia coli* for expression, so as to obtain double mutant MTHase.

$OD_{600\ nm}$ of shake flask culture for 24 h and enzyme activity of the wild type MTHase (WT) and the double mutant are listed in Table 2. The results show that the mutant L202P/Y323G has higher enzyme activity than the wild type.

TABLE 2

OD$_{600\ nm}$ of shake flask and enzyme activity
of wild type MTHase and double mutant enzyme

| Enzyme | OD$_{600\ nm}$ | Enzyme activity (U/mL) |
|---|---|---|
| WT | 12.9 | 31.2 |
| L202P/Y323G | 13.1 | 47.7 |

Example 5: Preparation, Expression and Enzyme Activity Analysis of MTHase Triple Mutant By using the plasmid of the mutant L202P/Y323G constructed in Example 2 and Example 4 as a template for triple mutation and according to site-directed mutagenic primers designed in embodiment 2, site-directed mutagenesis is performed on the plasmid carrying the genes encoding the mutant L202P/Y323G through a rapid PCR technique, so as to construct a triple mutant L202P/L218D/Y323G. Sequencing is performed to identify whether the encoding genes of MTHase triple mutant are correct, and the plasmid with correct sequencing result is introduced into *Escherichia coli* for expression, so as to obtain triple mutant MTHase.

OD$_{600\ nm}$ of shake flask culture for 24 h and enzyme activity of the wild type MTHase (WT) and the triple mutant are listed in Table 3. The results show that the mutant has higher enzyme activity than the wild type.

TABLE 3

OD$_{600\ nm}$ of shake flask and enzyme activity
of wild type MTHase and triple mutant enzyme

| Enzyme | OD$_{600\ nm}$ | Enzyme activity (U/mL) |
|---|---|---|
| WT | 12.9 | 31.2 |
| L202P/L218D/Y323G | 12.9 | 59.4 |

Example 6: Preparation, Expression and Enzyme Activity Analysis of MTHase Quadruple Mutant By using the plasmid of the triple mutant L202P/L218D/Y323G constructed in Example 5 as a template for quadruple mutant and according to site-directed mutagenic primers designed in Example 2, site-directed mutagenesis is performed on the plasmid carrying the genes encoding the mutant L202P/L218D/Y323G through a rapid PCR technique, so as to construct a quadruple mutant M140L/L202P/L218D/Y323G. Sequencing is performed to identify whether the encoding genes of MTHase quadruple mutant are correct, and the plasmid with correct sequencing result is introduced into *Escherichia coli* for expression, so as to obtain quadruple mutant MTHase.

OD$_{600\ nm}$ of shake flask culture for 24 h and enzyme activity of the wild type MTHase (WT) and the quadruple mutant are listed in Table 4. The results show that the mutant has higher enzyme activity than the wild type.

TABLE 4

OD$_{600\ nm}$ of shake flask and enzyme activity of
wild type MTHase and quadruple mutant enzyme

| Enzyme | OD$_{600\ nm}$ | Enzyme activity (U/mL) |
|---|---|---|
| WT | 12.9 | 31.2 |
| M140L/L202P/L218D/Y323G | 12.9 | 64.3 |

Example 7: Preparation, Expression and Enzyme Activity Analysis of MTHase Quintuple Mutant By using the plasmid of the mutant M140L/L202P/L218D/Y323G constructed in Example 2 as a template for quintuple mutant and according to site-directed mutagenic primers designed in Example 2, site-directed mutagenesis is performed on the plasmid carrying the genes encoding the mutant M140L/L202P/L218D/Y323G through a rapid PCR technique, so as to construct a quintuple mutant M140L/L202P/L218D/Y323G/F338S. Sequencing is performed to identify whether the encoding genes of MTHase quintuple mutant are correct, and the plasmid with correct sequencing result is introduced into *Escherichia coli* for expression, so as to obtain quintuple mutant MTHase.

OD$_{600\ nm}$ of shake flask culture for 24 h and enzyme activity of the wild type MTHase (WT) and the quintuple mutant are listed in Table 5. The results show that the mutant has higher enzyme activity than the wild type.

TABLE 5

OD$_{600\ nm}$ of shake flask and enzyme activity of
wild type MTHase and quintuple mutant enzyme

| Enzyme | OD$_{600\ nm}$ | Enzyme activity (U/mL) |
|---|---|---|
| WT | 12.9 | 31.2 |
| M140L/L202P/L218D/Y323G/F338S | 11.6 | 60.4 |

Example 8: Preparation, Expression and Enzyme Activity Analysis of MTHase Sextuple Mutant By using the plasmid of the mutant M140L/L202P/L218D/Y323G/F338S constructed in Example 2 as a template for sextuple mutant and according to site-directed mutagenic primers designed in Example 2, site-directed mutagenesis is performed on the plasmid carrying the genes encoding the mutant M140L/L202P/L218D/Y323G/F338S through a rapid PCR technique, so as to construct a sextuple mutant M140L/L202P/L218D/Y323G/F338S/I404T. Sequencing is performed to identify whether the encoding genes of MTHase sextuple mutant are correct, and the plasmid with correct sequencing result is introduced into *Escherichia coli* for expression, so as to obtain sextuple mutant MTHase.

OD$_{600\ nm}$ of shake flask culture for 24 h and enzyme activity of the wild type MTHase (WT) and the sextuple mutant are listed in Table 6. The results show that the enzyme activity of the sextuple mutant is 2.4 times that of the wild type enzyme.

TABLE 6

OD$_{600\,nm}$ of shake flask and enzyme activity of wild type MTHase and sextuple mutant enzyme

| Enzyme | OD$_{600\,nm}$ | Enzyme activity (U/mL) |
|---|---|---|
| WT | 12.9 | 31.2 |
| M140L/L202P/L218D/Y323G/F338S/I404T | 12.6 | 74.9 |

Example 9: Affinity to Substrate and Trehalose Conversion Rate Analysis of MTHase Mutant M140L/L202P/L218D/Y323G/F338S/I404T The affinity of the wild type enzyme and the mutant M140L/L202P/L218D/Y323G/F338S/I404T to a maltohexose substrate at 60° C. is determined. Results are shown in Table 7.

The results show that, compared with the wild type enzyme (WT), the $K_m$ value of the mutant M140L/L202P/L218D/Y323G/F338S/I404T decreases to some extent, and the decrease of the $K_m$ value indicates that the affinity of the mutant to the substrate is enhanced.

TABLE 7

$K_m$ values of MTHase mutant

| Enzyme | $K_m$ (mM) |
|---|---|
| WT | 3.89 ± 0.34 |
| M140L/L202P/L218D/Y323G/F338S/I404T | 3.4 ± 0.94 |

In the trehalose synthesis process, 150 g/L maltodextrin (DE value of 5-7) is used as a substrate, the initial pH is adjusted to 5.5, then the pullulanase (5 U/g starch) is added, and MTHase (20 U/g starch) and MTSase (80 U/g starch) at a ratio of 4 to 1 are added separately. The reaction conditions are 60° C. and 150 r/min. After reaction for 30 to 40 h, samples are boiled to terminate the reaction and undergo treatment. After the product is diluted and precipitated, the content of trehalose is determined by high performance liquid chromatography (HPLC) and the yield is calculated. HPLC detection conditions are as follows: mobile phase (acetonitrile:water=80:20); flow rate: 0.8 mL min$^{-1}$; column temperature: 40° C.; NH$_2$ column (APS-2 HYPERSIL, Thermo Scientific), and refractive index detector (RID). After calculation and analysis, it is shown that the conversion rate of wild type MTHase has reached 76.1%, while the conversion rate of mutant MTHase has reached 73.8%, which can be considered as no significant effect on the conversion rate of trehalose.

Example 10: Fermentation Enzyme Production Experiment of Mutant M140L/L202P/L218D/Y323G/F338S/I404T in 3L Fermenters 1) Seed activation: The preserved glycerol tubes is taken out from a −80° C. freezer, and an LB solid medium is inoculated with a small amount of bacteria solution by streak inoculation with inoculation needles, then incubation is performed in a 37° C. thermostatic incubator for 10-12 h. A single colony is selected, an LB liquid medium is inoculated with the single colony, and culture is performed at 37° C., and 200 r·min$^{-1}$ for 8-10 h.

2) Seed culture: 100 μL of the above activated bacterial solution is drawn, a 50 mL seed fermentation medium is inoculated with the bacterial solution, and culture is performed at 37° C., and 200 r·min$^{-1}$ for 8 h.

3) Culture in 3 L fermenter: NBS 3L full-automatic fermenters are used, with initial liquid volume of 1.2 L. The seed liquid obtained in the previous step is fed into a fermenter with an inoculation amount of 8%, and antibiotics are added at the same time. The initial dissolved oxygen in the fermenter is set to 100%, the initial rotation speed is set to 300 r min$^{-1}$, and pH is set to 7.0. After seeding, the dissolved oxygen in the fermenter is coupled with the rotation speed to maintain the dissolved oxygen in the fermenter at about 30%. After inoculation for 7 to 8 hours, the carbon source in the fermenter is used up and the dissolved oxygen rebounds, at this time, feed solution is added for feeding at a specific growth rate μ=0.2 h$^{-1}$. Samples are taken every 3 hours. The pH is adjusted by adding 25% aqueous ammonia to maintain the pH in the fermenter at 6.8 to 7.2 during the whole fermentation process. When the OD$_{600}$ reaches 50, the induction temperature is controlled at 30° C. and lactose is added for induction at a flow rate of 0.1 g·L$^{-1}$·h$^{-1}$.

Figure 1:
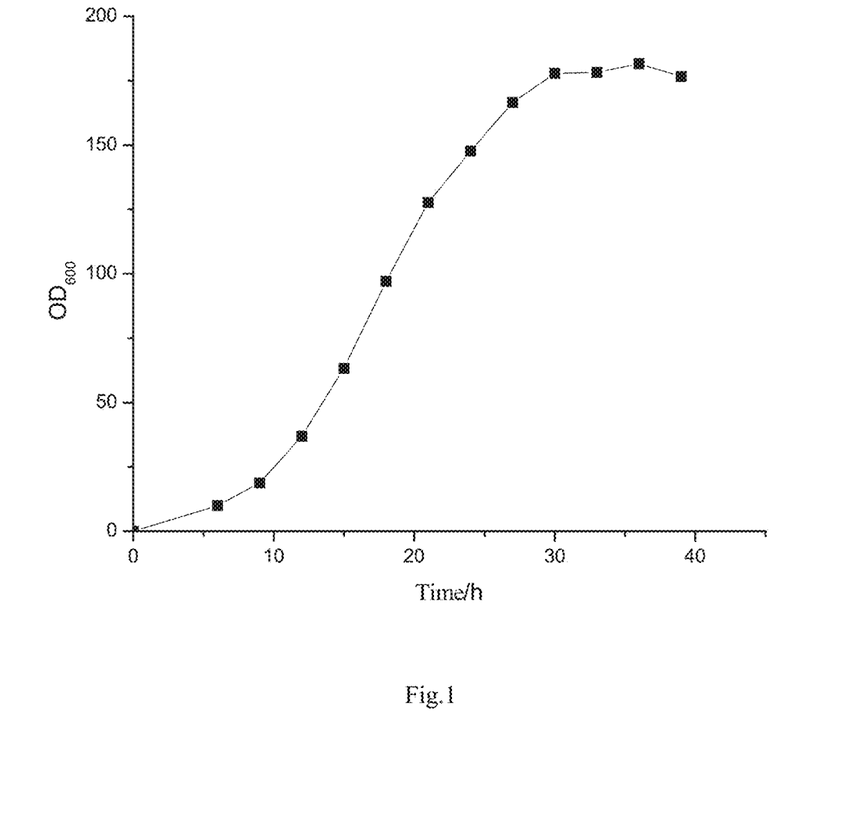
FIG. 1 shows the growth conditions of a mutant MTHase.
Figure 2:
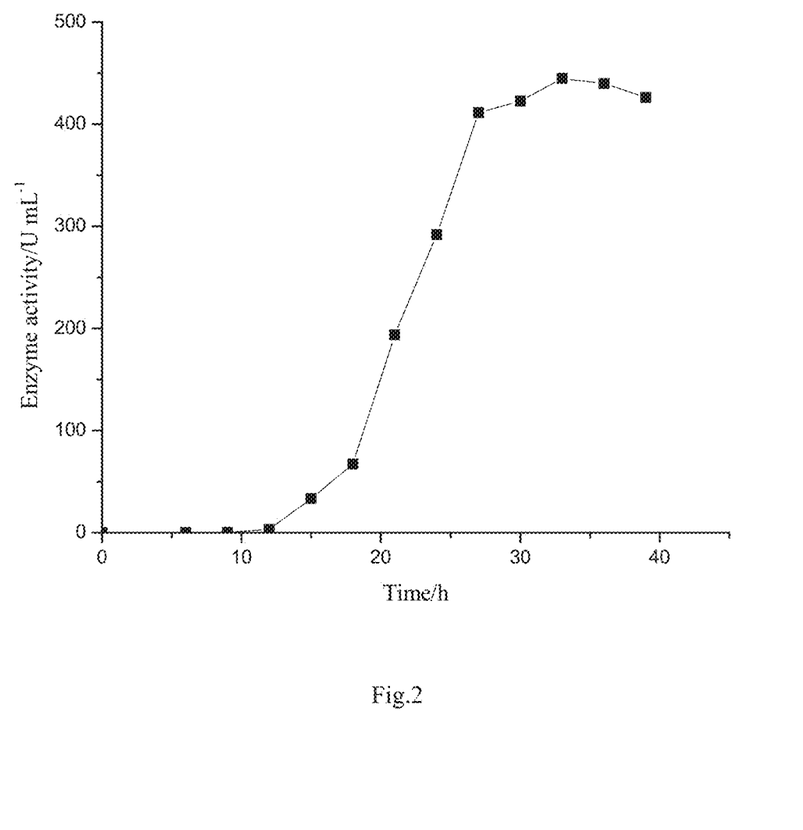
FIG. 2 shows the enzyme activity of a mutant MTHase.

Example 11: Fermentation Growth and Enzyme Production Effect of Mutant M140L/L202P/L218D/Y323G/F338S/I404T The bacteria are induced to produce target protein in a 3L fermenter under the conditions of induction temperature of 30° C., cell concentration OD$_{600}$ of 50, and inducer concentration (flow rate of lactose of 0.1 g·L$^{-1}$·h$^{-1}$). Results are shown in FIG. 1. The growth rate of bacteria is good at OD$_{600}$ of 50, and the flow rate of lactose has no significant effect on the bacteria growth. The maximum value of bacteria OD$_{600}$ is 181.5. The corresponding enzyme activity assay results are shown in FIG. 2. The maximum enzyme activity is 444.8 U·mL$^{-1}$. The maximum enzyme activity of wild type MTHase is 82 U·mL$^{-1}$ under the above condition, and the modification effect of the mutant MTHase is significant, and is increased by about 5 times.

What is claimed is:

1. A mutant of an isolated maltooligosyl trehalose trehalohydrolase, consisting of mutations compared with the amino acid sequence of a parent maltooligosyl trehalose trehalohydrolase obtained from *Sulfolobus acidocaldarius* as set forth in SEQ ID NO.2, wherein the mutations are selected from the group consisting of:

mutation of methionine (Met) at position 140 to leucine (Leu), and the mutant is named M140L;

mutation of leucine (Leu) at position 202 to proline (Pro), and the mutant is named L202P;

mutation of leucine (Leu) at position 218 to aspartic acid (Asp), and the mutant is named L218D;

mutation of phenylalanine (Phe) at position 338 to serine (Ser), and the mutant is named F338S;

mutation of isoleucine (Ile) at position 404 to threonine (Thr), and the mutant is named 1404T;

mutation of leucine (Leu) at position 202 to proline (Pro), and mutation of tyrosine (Tyr) at position 323 to glycine (Gly), and the mutant is named L202P/Y323G;

mutation of leucine (Leu) at position 202 to proline (Pro), mutation of leucine (Leu) at position 218 to aspartic acid (Asp), and mutation of tyrosine (Tyr) at position 323 to glycine (Gly), and the mutant is named L202P/L218D/Y323G;

mutation of methionine (Met) at position 140 to leucine (Leu), mutation of leucine (Leu) at position 202 to proline (Pro), mutation of leucine (Leu) at position 218 to aspartic acid (Asp), and mutation of tyrosine (Tyr) at position 323 to glycine (Gly), and the mutant is named M140L/L202P/L218D/Y323G;

mutation of methionine (Met) at position 140 to leucine (Leu), mutation of leucine (Leu) at position 202 to proline (Pro), mutation of leucine (Leu) at position 218 to aspartic acid (Asp), mutation of tyrosine (Tyr) at position 323 to glycine (Gly), and mutation of phenylalanine (Phe) at position 338 to serine (Ser), and the mutant is named M140L/L202P/L218D/Y323G/F338S; and mutation of methionine (Met) at position 140 to leucine (Leu), mutation of leucine (Leu) at position 202 to proline (Pro), mutation of leucine (Leu) at position 218 to aspartic acid (Asp), mutation of tyrosine (Tyr) at position 323 to glycine (Gly), mutation of phenylalanine (Phe) at position 338 to serine (Ser), and mutation of isoleucine (Ile) at position 404 to threonine (Thr), and the mutant is named M140L/L202P/L218D/Y323G/F338S/I404T; and wherein the mutant has increased enzymatic activity of maltooligosyl trehalose trehalohydrolase compared to the parent maltooligosyl trehalose trehalohydrolase.

2. An isolated polynucleotide encoding the mutant of claim 1.

3. A vector or an isolated recombinant cell carrying the isolated polynucleotide of claim 2.

4. A method for preparing the mutant of claim 1, comprising the following steps:
   (1) designing a site-directed mutagenic primer based on a determined mutation site, and carrying out site-directed mutagenesis by using a vector carrying a maltooligosyl trehalose trehalohydrolase gene as a template; constructing a plasmid vector containing the gene encoding the mutant;
   (2) transforming a mutant plasmid into a host cell; and
   (3) picking out a positive clone for fermentation, and collecting cells by centrifugation, wherein cell wall breaking supernatant is a crude enzyme solution of the mutant maltooligosyl trehalose trehalohydrolase.

5. A method for producing the mutant of claim 1, comprising: inoculating a fermentation medium with a recombinant *Escherichia coli* expressing the mutant of claim 1, culturing at 37° C. for 8 to 14 hours, adding lactose at a flow rate of 0.1 g $L^{-1}$ $h^{-1}$, and performing induction at 30° C. for 10 to 20 hours.

6. The method of claim 5, wherein the fermentation medium per liter contains 4.0 g of diammonium phosphate, 13.5 g of potassium dihydrogen phosphate, 1.7 g of citric acid, 1.4 g of magnesium sulfate heptahydrate, 1.2 g of peptone, 2.4 g of yeast extract, 8.0 g of glycerol, and 10 mL of metal ion liquid, and the pH is adjusted to 6.5 to 7.5.

7. An enzyme preparation for producing trehalose, comprising the mutant of claim 1.

* * * * *